US00PP20479P3

(12) United States Plant Patent
Sanders

(10) Patent No.: US PP20,479 P3
(45) Date of Patent: Nov. 17, 2009

(54) *AGERATUM* PLANT NAMED 'AGADEFT'

(50) Latin Name: *Ageratum houstonianum*
Varietal Denomination: Agadeft

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/006,541

(22) Filed: Jan. 3, 2008

(65) Prior Publication Data

US 2009/0178172 P1 Jul. 9, 2009

(51) Int. Cl.
*A01H 5/00* (2006.01)

(52) U.S. Cl. ..... Plt./400

(58) Field of Classification Search ..... Plt./400
See application file for complete search history.

*Primary Examiner*—Annette H Para
*Assistant Examiner*—Louanne C Krawczewicz Myers
(74) *Attorney, Agent, or Firm*—S. Matthew Edwards

(57) ABSTRACT

A new *Ageratum* plant named 'Agadeft' particularly distinguished by its large, near white capitula with mid violet stigma when opening, its early flowering, its strong branching and vigorous growth.

1 Drawing Sheet

Latin name of the genus and species of the plant claimed: *Ageratum houstonianum.*

Varietal denomination: 'Agadeft'.

BACKGROUND OF THE NEW PLANT

The present invention comprises a new and distinct cultivar of *Ageratum,* botanically known as *Ageratum houstonianum,* and herinafter referred to by the cultivar name 'Agadeft.' The new cultivar is propagated from cuttings, resulting from a cross-pollination in September 2002 of a proprietary selection of *Ageratum houstonianum* identified as number 'W52-7,' not patented, as the female, or seed parent, with a proprietary selection of *Ageratum houstonianum* identified as number 'X12-3,' not patented, as the male, or pollen parent.

As a result, the present cultivar was found in 2003 in Enkhuizen, Netherlands and has been repeatedly asexually reproduced by cuttings in Enkhuizen, Netherlands, in Gilroy, Calif., USA, in Angers, France and in Sarrians, France since 2003.

The distinctive characteristics of this new *Ageratum* are stable and reproduced true to type in successive generations of asexual reproduction. It takes 7 to 9 weeks to produce a finished plant, depending on the temperature.

This new *Ageratum* plant is an annual in most climatic zones in the U.S. It is a perennial plant only in zones 9 and 10.

SUMMARY OF THE INVENTION

The following traits have been repeatedly observed and are determined to be the unique characteristics of 'Agadeft.' These characteristics in combination distinguish 'Agadeft' as a new and distinct *Ageratum* cultivar:

1. Vigorous, upright and mounded growth habit
2. Freely branching habit
3. Freely flowering habit with many large capitula in compound umbels
4. Near white capitula that turn mid violet when flowers open
5. Medium sized, green colored leaves Plants of the new *Ageratum* differ primarily from plants of the female parent selection in the following characteristics:

Plants of the new *Ageratum* have near white capitula with mid violet stigma whereas plants of the female parent selection have near white flowers.

Plants of the new *Ageratum* differ primarily from plants of the male parent selection in the following characteristics:

Plants of the new *Ageratum* have near white capitula with mid violet stigma whereas plants of the male parent selection have mid violet flowers.

TABLE 1

DIFFERENCES BETWEEN THE NEW CULTIVAR 'AGADEFT' AND A SIMILAR CULTIVAR

| | 'AGADEFT' | 'AGALIB' (U.S. Plant Pat. No. 17,117) |
|---|---|---|
| Number of disk florets per capitulum | 140 | 85 |
| Color of capitulum at full flowering | RHS N157A | RHS 92B |

BOTANICAL DESCRIPTION OF THE PLANT

The following detailed descriptions set forth the distinctive characteristics of this new *Ageratum.* The data which define these characteristics were collected from asexual reproductions carried out in Enkhuizen, Netherlands. The plant history was taken on plants of 30 weeks old, blossomed under natural light and artificial light in a greenhouse.

Color readings were taken in laboratory under ambient light. Color references are primarily to The R.H.S. Color Chart of The Royal Horticultural Society of London.

The plant:

*Classification — botanical.—Ageratum houstonianum.*

Parentage:

*Female parent.*—Proprietary selection 'W52-7,' not patented.

*Male parent.*—Proprietary selection 'X12-3,' not patented.

Plant description:

*Growth habit.*—Upright.

*Branching habit.*—Freely branching; lateral branches at every node.

*Plant height.*—24 cm.

*Spreading area of plant.*—44 cm.

*Vigour.*—Strong.

*Strength.*—Very strong.

*Blooming period.*—Year round.

The stem:

*Length.*—27 cm.

*Diameter.*—4 mm.

*Shape of cross section.*—Round.

*Color.*—RHS 145A.

*Anthocyanin pigmentation.*—Absent.

*Internode length.*—35–40 mm, depending on light intensity.

*Pubescence.*—Slightly pubescent.

The foliage:

*Phyllotaxis.*—Opposite, decussate.

*Shape of blade.*—Ovate.

*Texture upper and lower side.*—Slightly pubescent.

*Venation.*—Reticulate.

*Leaf margin.*—Serrate.

*Leaf base.*—Cordate.

*Leaf apex.*—Acute.

*Length.*—39 mm.

*Width.*—38 mm.

*Color upper side.*—RHS 137A.

*Color lower side.*—RHS 137C.

*Vein color upper surface.*—RHS 144A basally, becoming more distinct towards apex.

*Vein color lower surface.*—RHS 144B.

*Pubescence.*—Slightly pubescent.

*Petiole.*—Length: 12 mm Diameter: 2 mm Color: RHS 138C Texture: Slightly pubescent.

The inflorescence:

*Inflorescence type.*—Compound umbel of capitula.

*Number of inflorescences per plant.*—90–100.

*Inflorescence depth (length).*—0.7–0.9 cm.

*Inflorescence diameter.*—1.0–1.2 cm.

*Receptacle depth (length).*—0.5 cm.

*Receptacle diameter.*—0.5–0.7 cm.

*Umbel width.*—4.1 cm.

*Umbel depth.*—2.2 cm.

*Peduncle length.*—22 mm.

*Peduncle diameter.*—2 mm.

*Peduncle color.*—RHS 144A.

*Pedicel length.*—4 mm.

*Pedicel diameter.*—1 mm.

*Pedicel color.*—RHS 144B.

*Number of capitula per inflorescence.*—7–9.

*Number of disc florets per capitulum.*—Approximately 140.

*Number of ray florets per capitulum.*—0.

*Flower buds.*—Length (depth): 0.5 cm Diameter: 0.7–0.9 cm just before opening Color: RHS 157C just before stigmas appear.

*Shape.*—Oblate with a flat top.

*Disk florets.*—Corolla shape: Actinomorphic Number of lobes: 5 Apex: 5 lobbed, obtuse lobes. Base: Round Margins: Entire Length: 1.5 mm Diameter: 1 mm Color upper side: RHS N155A Color lower side: RHS 155B.

*Phyllaries.*—Number of phyllaries per capitulum: 19 Length: 5 mm Diameter: 0.5 mm Shape: Elliptical Apex: Acumate Base: Attenuate Receptacle: Conical Margins: Entire Texture upper surface: Smooth Texture lower/under surface: Hirsute Color outer side: RHS 138A with tip RHS 184A Color inner side: RHS 138B with tip RHS 184B.

*Capitulum.*—Diameter at begin of flowering: 6 mm Diameter at full flowering: 25–30 mm Depth: 5 mm Color at begin of flowering: RHS N155A. Color at full flowering: RHS N157A.

*Lastingness of the bloom.*—The capitula of one umbel open over a period of 3–4 weeks.

Reproductive organs:

*Number of pistils.*—1.

*Pistil shape.*—Style with two filiform branches.

*Pistil length.*—6–7 mm.

*Stigma color.*—RHS N88A.

*Quantity of styles.*—Approximately 100.

*Style length.*—About 0.2 cm.

*Style color.*—Closest to RHS N155 but a little whiter.

*Ovary type.*—Inferior; 5 ribbed.

*Ovary color.*—RHS 155A.

*Pappus.*—Coroniform.

*Number of anthers.*—5, connate in a tube, filaments free.

*Shape of anthers.*—Ecalcarate.

*Pollen amount.*—Small.

*Pollen color.*—RHS N155A.

*Fragrance.*—Absent.

Seed development: Some seed development has been observed on plants of the new *Ageratum.*

*Seed shape.*—Pentagonal.

*Seed length.*—2 mm.

*Seed diameter.*—0.8 mm.

*Seed color.*—RHS 202A.

Roots:

*Type of roots.*—Fibrous. Roots start to grow on every part of the stem that contacts the soil, so not only at the nodes.

Disease/pest resistance: No disease/pest resistance has been observed to date.

Temperature tolerance: Plants of the new *Ageratum* have been observed to be tolerant to temperatures ranging from 4 to 30° C.

What is claimed is:

1. A new and distinct variety of *Ageratum* plant named 'Agadeft', as substantially illustrated and described herein.

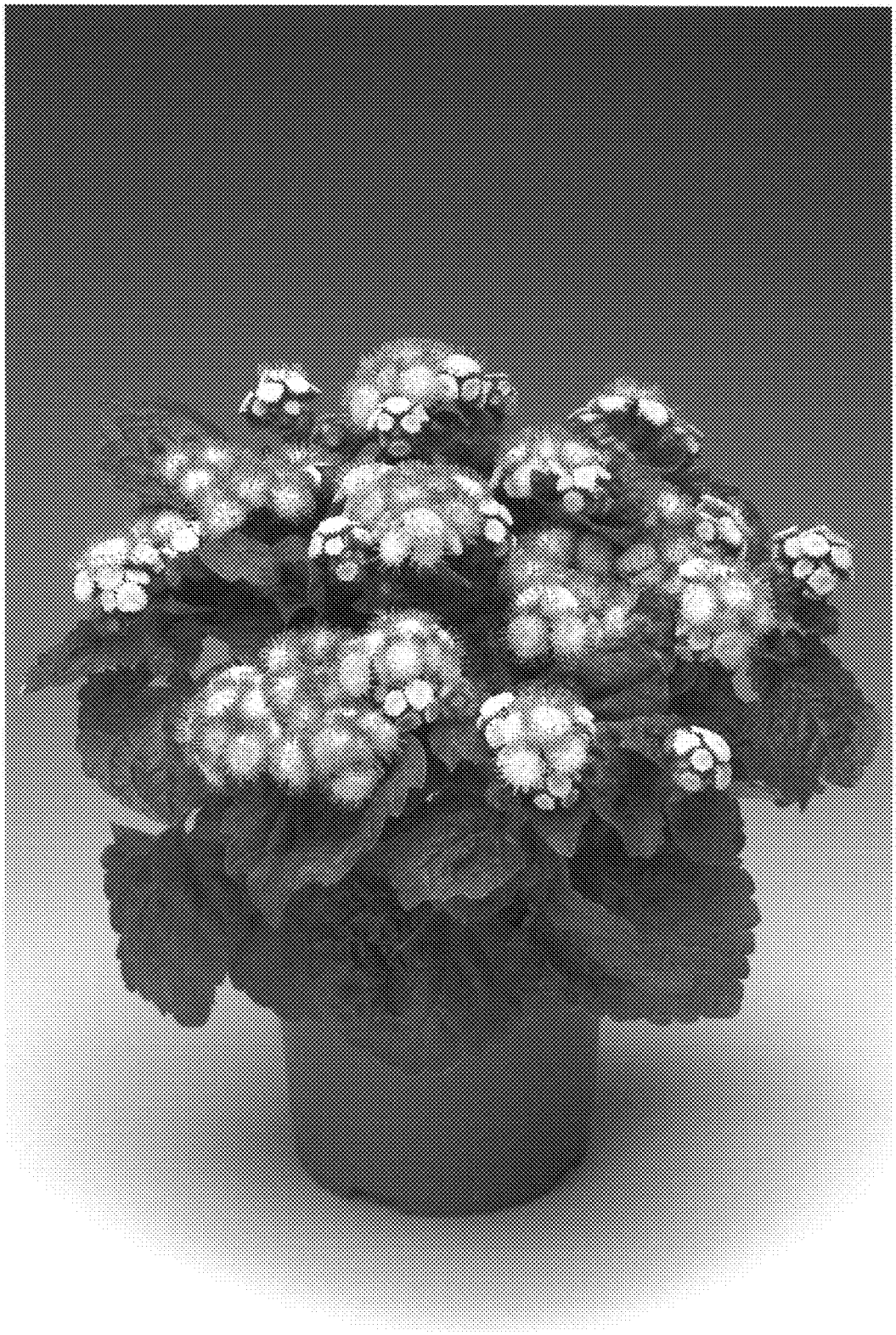

* * * * *